United States Patent
Bureau

(10) Patent No.: US 9,322,806 B2
(45) Date of Patent: Apr. 26, 2016

(54) EDDY CURRENT SENSOR WITH LINEAR DRIVE CONDUCTOR

(71) Applicant: General Electric Company, Schenectady, NY (US)

(72) Inventor: Jean-Francois Bureau, St-Jerome (CA)

(73) Assignee: General Electric Company, Schenectady, NY (US)

( * ) Notice: Subject to any disclaimer, the term of this patent is extended or adjusted under 35 U.S.C. 154(b) by 128 days.

(21) Appl. No.: 14/063,749

(22) Filed: Oct. 25, 2013

(65) Prior Publication Data

US 2015/0115945 A1 Apr. 30, 2015

(51) Int. Cl.
*G01N 27/90* (2006.01)

(52) U.S. Cl.
CPC .................................. *G01N 27/9033* (2013.01)

(58) Field of Classification Search
CPC ........................................................ G01N 27/90
USPC ........................................................ 324/239
See application file for complete search history.

(56) References Cited

U.S. PATENT DOCUMENTS

| 3,967,193 | A | 6/1976 | Bergstrand |
| 5,262,722 | A | 11/1993 | Hedengren et al. |
| 5,389,876 | A | 2/1995 | Hedengren et al. |
| 6,271,655 | B1 * | 8/2001 | Weber et al. ............. 324/117 R |
| 6,784,662 | B2 | 8/2004 | Schlicker et al. |
| 6,995,557 | B2 | 2/2006 | Goldfine et al. |
| 7,049,811 | B2 | 5/2006 | Schlicker et al. |
| 2005/0140355 | A1 | 6/2005 | Yamada et al. |
| 2012/0019239 | A1 | 1/2012 | Decitre |
| 2013/0138372 | A1 * | 5/2013 | Ausserlechner ............... 702/65 |

FOREIGN PATENT DOCUMENTS

FR 2944354 A1 10/2010

OTHER PUBLICATIONS

European Search Report and Opinion issued in connection with corresponding EP Application No. 14189946.8 on Feb. 27, 2015.

* cited by examiner

*Primary Examiner* — Bot Ledynh
(74) *Attorney, Agent, or Firm* — Barclay Damon, LLP

(57) ABSTRACT

A multi-layer eddy current sensor includes a sense coil for detecting an eddy current, and a drive conductor for inducing the eddy current. The drive conductor comprises a substantially straight conducting portion that traverses the entire width of the sense coil.

14 Claims, 5 Drawing Sheets

EDDY CURRENT SENSOR WITH LINEAR DRIVE CONDUCTOR

BACKGROUND OF THE INVENTION

The subject matter disclosed herein relates to multi-layer sensors used in eddy current probes and, in particular, to a sensor design having a linear drive conductor.

Eddy current probes are a form of nondestructive test devices that can be used to inspect test objects made of electrically conductive material to detect and analyze flaws in the test objects. Nondestructive testing allows an inspection technician to maneuver an eddy current probe over a surface of the test object during a test scan.

In an eddy current sensor, a magnetic field is used to induce an electrical current in the test object. The magnetic field is typically generated by one or more drive circuits typically in the form of electrically conductive drive coils, or windings, in the eddy current sensor. During operation of the probe, an electrical current travels through the drive coil, or coils, which generates a magnetic field that passes into the test object and induces an electrical current in the test object called an eddy current. The eddy current in the test object will itself generate a detectable magnetic field. This responsive magnetic field is then detected by a sense coil, or coils, and is analyzed by programmed electronics in the eddy current probe.

If the induced eddy current passes through a flaw or defect in the test object during the scan, the induced eddy current is perturbed and the sense coils will detect this as a varying impedance. In response to detecting the varying impedance, the sense coils will generate electrical signals that represent physical characteristics of the defect. By analyzing these electrical signals, various characteristics of the defect (e.g., location, size) can be determined. The impedance difference detected by the sense coils can be converted into a two-dimensional impedance data display.

Typical eddy current sensors utilize complementary, multi-turn coils in driving and sensing circuits which together form a relatively large footprint and are sensitive to noise effects caused by scanning edges of the test object.

The discussion above is merely provided for general background information and is not intended to be used as an aid in determining the scope of the claimed subject matter.

BRIEF DESCRIPTION OF THE INVENTION

A multi-layer eddy current sensor includes a sense coil for detecting an eddy current, and a drive conductor for inducing the eddy current. The drive conductor comprises a substantially straight conducting portion that traverses the entire width of the sense coil. An advantage that may be realized in the practice of some disclosed embodiments of the eddy current sensor probe is that the drive circuit generates a self nulling magnetic field in the sense coil which reduces noise, and the overall footprint of the eddy current sensor is smaller. Interference from an edge of the test object is reduced, resulting in improved edge inspection.

In one embodiment, an eddy current sensor is disclosed. The eddy current sensor includes a first sense coil for detecting an eddy current, wherein the first sense coil comprises a first axis and a first width. The eddy current sensor also includes a first drive conductor for inducing the eddy current, the first drive conductor spaced apart from the first sense coil by an insulator layer. The first drive conductor includes a substantially straight conducting portion that traverses the first width of the first sense coil.

In another embodiment, the eddy current sensor includes a first plurality of sense coils for detecting an eddy current, wherein each of the first plurality of sense coils is disposed in a first layer of the eddy current sensor and arranged in a first row therein, each of the first plurality of sense coils comprising a first axis and a first width. The eddy current sensor also includes a first drive conductor for inducing the eddy current, wherein the first drive conductor is disposed in a second layer of the eddy current sensor and spaced apart from the first plurality of sense coils by an insulator layer. The first drive conductor comprises a substantially straight conducting portion that traverses each of the first widths of the first plurality of sense coils in the first row.

In yet another embodiment, the eddy current sensor includes a first sense coil for detecting an eddy current, wherein the first sense coil comprises a first axis and a first width. The eddy current sensor also includes a first drive conductor for inducing the eddy current, the first drive conductor spaced apart from the first sense coil by an insulator layer, wherein the first drive conductor comprises a substantially straight conducting portion that traverses the width of the first sense coil on a first longitudinal axis. In addition, the eddy current sensor includes a second drive conductor for inducing the eddy current, the second drive conductor spaced apart from the first sense coil by the insulator layer, wherein the second drive conductor comprises a substantially straight conducting portion that traverses the width of the first sense coil on a second longitudinal axis.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
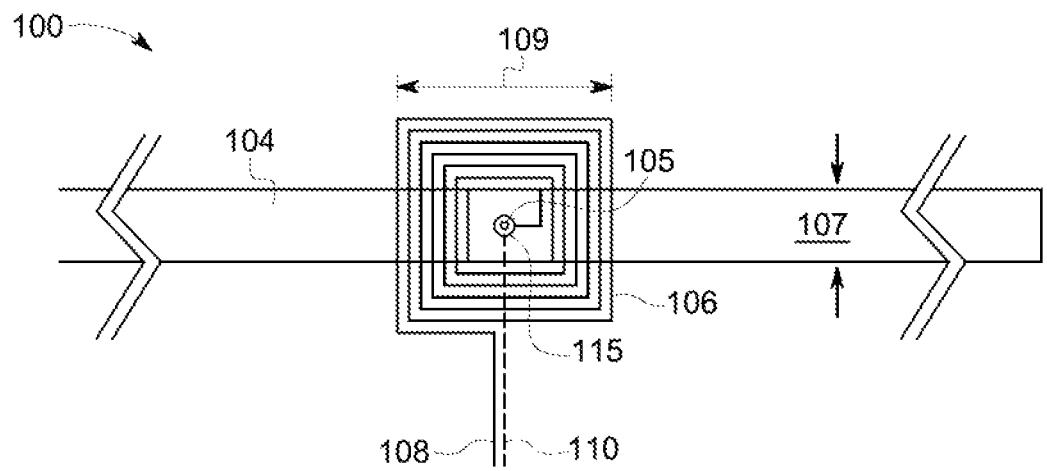
FIG. 1 is a diagram of an exemplary eddy current sensor with a linear drive conductor.

FIG. 1 illustrates a top view of an exemplary embodiment of an eddy current sensor 100 including a drive conductor 104 and a first sense coil 106. The eddy current sensor 100 may be used to construct an eddy current probe having one or more of the eddy current sensors 100 formed therein. The overall construction of the eddy current sensor 100 utilizes a multi-layer flexible printed circuit. The drive conductor 104 is formed in one layer of the flexible printed circuit while the first sense coil 106 is formed in another layer thereof. The drive conductor 104 may be formed in a substantially straight line in the portion of the drive conductor 104 that traverses the width 109 of the first sense coil 106. The drive conductor 104 may have a width 107 ranging from about 0.25 mm to over about 8.0 mm. The sense coil may be formed in one or more layers of the multi-layer printed circuit, as will be explained below. A width 109 of the first sense coil 106 may vary from about 1.0 mm to over about 5.0 mm as measured at the outermost edges of the first sense coil 106. In one embodiment, the width 109 of the first sense coil 106 is about 1.6 mm and the width 107 of the drive conductor 104 is about 0.38 mm. A center of the first sense coil 106 comprises an axis 105 that is perpendicular to a plane containing the first sense coil 106. In one embodiment, the drive conductor 104 and the first sense coil 106 are positioned, in their respective layers of the multi-layer printed circuit, such that the axis 105 of the first sense coil 106 intersects the drive conductor 104, as illustrated in FIG. 1. In one embodiment, the first sense coil 106 is positioned vertically below the drive conductor 104, in their respective layers of the multi-layer printed circuit, such that the first sense coil 106 is situated between the drive conductor 104 and the test object during a scan of the test object. In another embodiment, the drive conductor 104 is positioned vertically below the first sense coil 106, in their respective layers of the multi-layer printed circuit as illustrated in FIG. 1, such that the drive conductor 104 is situated between the first sense coil 106 and the test object during a scan of the test object.

The first sense coil 106 terminates at electrical leads 108, 110 which may be connected to electronics of an eddy current probe for performing test scans. The drive conductor 104 is similarly connected to the eddy current probe, wherein the eddy current probe controllably drives an electric current, having a selected magnitude and frequency, through the drive conductor 104. The electrical lead 108 is formed in a same layer of the multi-layer printed circuit as the first sense coil 106. Electrical lead 110 is formed in a different layer of the multi-layer printed circuit than the electrical lead 108, and is electrically connected to first sense coil 106 by a via 115. As will be described in more detail below, the multi-layered printed circuit generally comprises variously alternating layers of an insulator, an adhesive, and a conductor. The conductor layers of the multi-layer printed circuit comprise the drive conductor 104 and the first sense coil 106 just described.

As explained above, an eddy current probe drives an electric current at a selected frequency and amplitude through the drive conductor 104 to induce an eddy current in a test object for performing a scan thereof. The induced eddy current in the test object generates a measurable magnetic field that is detected by the first sense coil 106. This detection is made more sensitive with an increased number of windings in the first sense coil 106. Each turn, or winding, of the first sense coil 106 detects the magnetic field by generating a small voltage in response to the eddy current magnetic field, such that each turn of the coil contributes (adds) an amount of voltage to an overall sense coil voltage signal which can then be analyzed by electronics of the eddy current probe. In one embodiment, a width of each winding of the first sense coil 106 is about 0.05 mm with an equivalent spacing between the windings. Thus, with about six turns in a planar, square shaped first sense coil 106, the overall width 109 of the first sense coil 106 is equal to about 1.6 mm, as illustrated in the first sense coil 106 of FIG. 1. If the windings of the first sense coil 106 have a smaller width of about 0.025 mm with an equivalent spacing between turns of the first sense coil 106, the number of turns would increase by about 2×, thereby increasing the sensitivity of the first sense coil 106.

Figure 2:
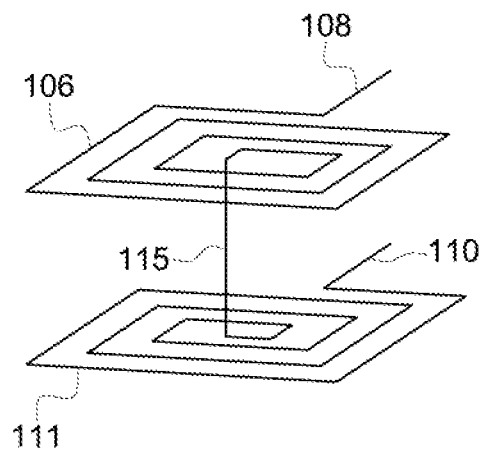
FIG. 2 is a diagram of two exemplary sense coils electrically connected.

FIG. 2 shows an isolated view of one embodiment of the eddy current sensor 100 wherein a first sense coil 106 is electrically connected to a second sense coil 111. Each of the sense coils 106, 111 is formed in a separate layer of a flexible multi-layer printed circuit, and are electrically connected by a via 115 formed through an intervening layer of the multi-layer printed circuit, which intervening layer may be an insulator layer. Electrical lead 108 is formed in the same layer of the multi-layer printed circuit as the first sense coil 106, while electrical lead 110 is formed in the same layer of the multi-layer printed circuit as the second sense coil 111. The insulator layer, which will be described in more detail below, maintains the sense coils 106, 111 in a vertical, substantially parallel, spaced apart relationship, as illustrated in FIG. 2.

Figure 3:
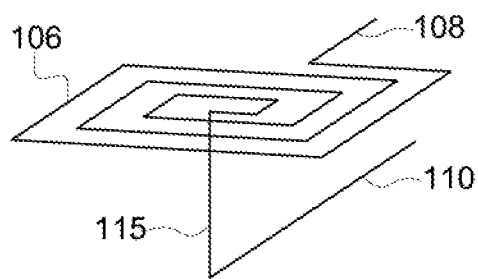
FIG. 3 is a diagram of an exemplary single sense coil.

FIG. 3 shows an isolated view of one embodiment of the eddy current sensor 100 comprising a first sense coil 106 electrically connected to electrical lead 108 formed in the same layer of the multi-layer printed circuit as the first sense coil 106, and to electrical lead 110 formed in a separate layer of the multi-layer printed circuit. The first sense coil 106 is electrically connected to electrical lead 110 by a via 115 formed through an intervening layer of the multi-layer printed circuit, which intervening layer may be an insulator layer.

Figure 4:
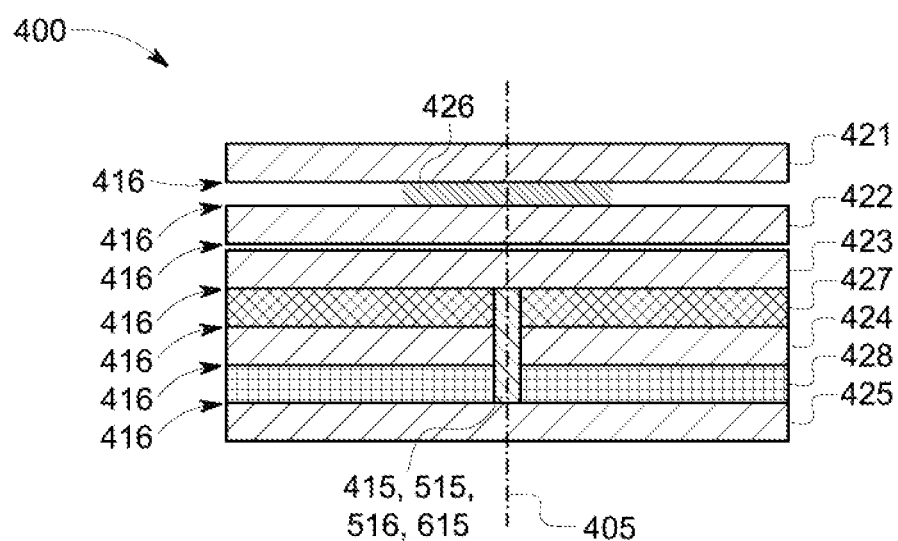
FIG. 4 is a diagram of an exemplary multi-layer printed circuit.

FIG. 4 illustrates an exemplary configuration of a flexible multi-layer printed circuit 400 arranged to create the eddy current sensor 100 as illustrated in FIG. 1. The multi-layer printed circuit 400 comprises insulator layers 421-425, conductor layers 426-428, and adhesive layers 416. The thickness of the adhesive layers 416 are shown in minimized form for ease of illustration in the Figure, however, the thickness of the adhesive layers 416 is similar to that of the insulator layers 421-425, which may range from about 0.01 mm to about 0.1 mm. FIG. 4 may be considered as a generalized side view of the eddy current sensor 100, and is not drawn to specifically illustrate a cross-section of the eddy current sensor 100 of FIG. 1. The various layers 421-428 of the multi-layer printed circuit of FIG. 4 may be referred to throughout the present disclosure to provide a structural reference for the various embodiments described herein.

An uppermost conductor layer 426 of the multi-layer printed circuit 400 comprises the drive conductor 104 described above. The conductor layer 426 may comprise one or more of drive conductors 104. Another conductor layer 427 comprises a first sense coil 106 formed as a planar, square shaped coil, within which layer 427 may also include an electrical lead 108 of the first sense coil 106 (FIGS. 1-3). One or more additional first sense coils 106 may be formed in conductor layer 427 each with a corresponding electrical lead 108. A person skilled in the art will appreciate that the sense coils 106 can have various configurations other than those shown, such as round, triangular, oval or other shape, and can include any combination of features disclosed herein and known in the art.

For embodiments as shown in FIG. 2, where a first sense coil 106 is electrically connected to a second sense coil 111 in a lower conductor layer 428 of the multi-layer printed circuit 400 (FIG. 4), the second sense coil 111, connected to electrical lead 110 formed in the same conductor layer 428 as the sense coil 111, is also connected to the first sense coil 106 by a via 415 formed between the conductor layers 427, 428 through an intervening insulator layer 424. The via 415 may be formed proximate to the axes 405 of the sense coils 106, 111. One or more additional second sense coils 111 may be formed in conductor layer 428, each with a corresponding electrical lead 110.

For embodiments as shown in FIG. 3, where a first sense coil 106 is not electrically connected to a second sense coil 111 in a lower conductor layer 428 of the multi-layer printed circuit 400 (FIG. 4), electrical lead 110 formed in a lower conductor layer 428 of the multi-layer printed circuit is connected to the first sense coil 106 by a via 415 formed between the conductor layers 427, 428 through an intervening insulator layer 424. The via 415 may be formed proximate to the axis 405 of the first sense coil 106.

The insulator layers 421-425 are used to spatially separate and selectively electrically isolate the conductor layers 426-428 including the drive conductor 104 and the sense coils 106, 111 formed therein. The insulator layers 421-425 may be comprised of a polyimide such as Kapton tape, or Teflon tape. The conductor layers 426-428, used for forming the drive conductor 104 and the sense coils 106, 111, may comprise a metal such as copper formed by a deposition process or copper tape adhered between the insulator layers. The copper layers may comprise a thickness of about 5 μm. Adhesive layers 416 are placed between each insulator layer, 421-425, and each conductor layer 426-428. In one embodiment, each of the insulator layers 421-425 and the adhesive layers 416 may be about 0.013 mm thick. The conductor layers 426-428 may each be about 5 μm thick. As shown in FIG. 4, each of the layers 421-428 of the multi-layer printed circuit 400 may be individually fabricated and, as the layers 421-428 are stacked, secured in place using an adhesive coating or double-sided adhesive tape between each assembled layer 421-428.

Figure 5:
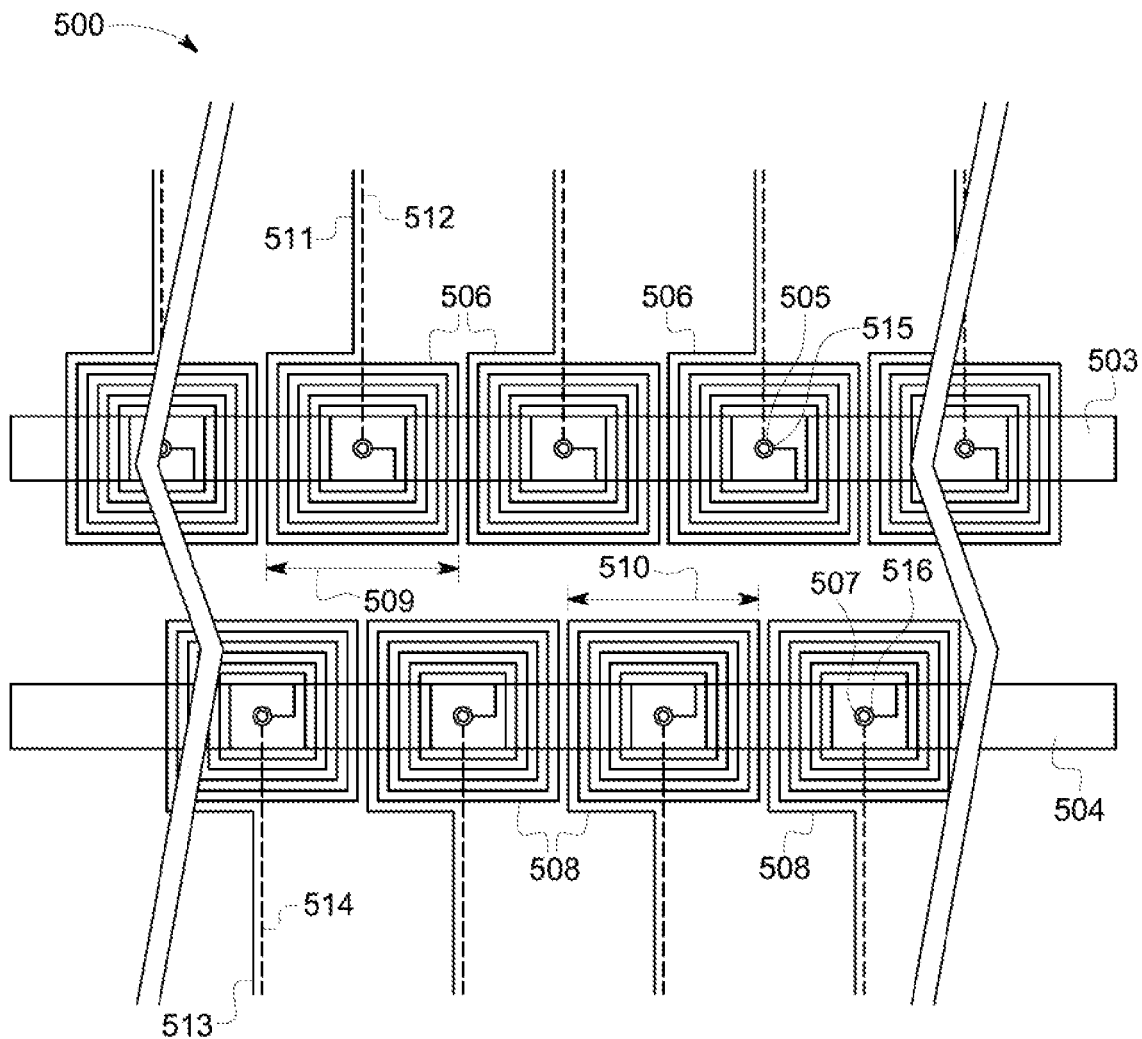
FIG. 5 is a diagram of an exemplary eddy current sensor array.

FIG. 5 illustrates an eddy current sensor array 500 comprising a first and second plurality of sense coils 506, 508 and a plurality of drive conductors 503, 504, operative as a plurality of individual eddy current sensors as described above with respect to FIG. 1. In the exemplary embodiment of FIG. 5, a first plurality of sense coils 506 are arranged in one row while a second plurality of sense coils 508 are arranged in a second row. Each of the first plurality of sense coils 506 in one row comprise an axis 505 and a width 509, while each of the second plurality of sense coils 508 in the second row comprise an axis 507 and a width 510. In one embodiment of the eddy current sensor array 500, two rows of sense coils 506, 508 each comprise sixty-four sense coils for a total of one hundred twenty eight eddy current sensors 100 (FIG. 1) in one eddy current probe. As explained above in relation to FIG. 1, the drive conductors 503, 504 and their corresponding sense coils 506, 508 may be formed in the multi-layer printed circuit with the sense coils 506, 508 vertically above their corresponding drive conductor 503, 504, or vice versa.

The first plurality of sense coils 506 are positioned with respect to the first drive conductor 503 such that each of their axes 505 intersect the first drive conductor 503 while the second plurality of sense coils 508 are positioned with respect to the second drive conductor 504 such that each of their axes 507 intersect the second drive conductor 504. The drive conductors 503, 504 may be formed in a substantially straight line over their entire length, i.e., over the entire combined widths 509, 510 of their corresponding sense coils 506, 508, respectively. In one embodiment, the drive conductors 503, 504 may be formed in a substantially straight line at least in the portion of the drive conductors 503, 504 that traverse the widths 509, 510 of the first and second plurality of sense coils 506, 508, respectively.

The first and second plurality of sense coils 506, 508 may be formed in the same conductor layer 427 of the multi-layer printed circuit (FIG. 4). The first and second plurality of sense coils sense coils 506, 508 are configured to detect eddy currents in a test object that are induced therein by the drive conductors 503, 504. The eddy current sensor array 500 comprises individual sense coils 506, 508 and corresponding drive conductors 503, 504 that cooperate in a similar fashion as the exemplary eddy current sensor 100, as explained above with reference to FIG. 1. Pairs of electrical leads 511, 512 are connected to each of the first plurality of sense coils 506 while pairs of electrical leads 513, 514 are connected to each of the second plurality of sense coils 508. The electrical leads 511-514 transmit voltage signals generated in their attached sense coils 506, 508 to electronics of an eddy current probe for analysis therein, such as for determining the location and size of a flaw in a scanned object.

In one embodiment, the first drive conductor 503 may be formed in one conductor layer 426 of the multi-layer printed circuit (FIG. 4), which operates in conjunction with the corresponding first plurality of sense coils 506 arranged in one row and formed in another conductor layer 427 of the multi-layer printed circuit. In another embodiment, the first and second drive conductors 503, 504 may be formed in the conductor layer 426 and each operated in conjunction with one corresponding row of sense coils 506, 508 as illustrated in FIG. 5. The plurality of rows of sense coils 506, 508 may be formed in a common conductor layer 427 of the multi-layer printed circuit 400.

In one embodiment of the eddy current sensor array 500, each of the sense coils 506, 508 may be formed as a single sense coil in one conductor layer 427 of the multi-layer printed circuit 400 (FIG. 4), as described above in relation to FIG. 3. In this embodiment, each of the sense coils 506, 508 are connected to electrical leads, 512, 514 in another conductor layer 428, respectively, by a via 515, 516, respectively, that passes through an intervening insulator layer 424.

In another embodiment of the eddy current sensor array 500, each of the sense coils 506, 508 may be formed as first and second sense coils formed in two separate conductor layers 427, 428 of the multi-layer printed circuit (FIG. 4), as described above in relation to FIG. 2. In this embodiment, the first sense coils are formed in conductor layer 427 and are each electrically connected to second sense coils formed in another conductor layer 428, respectively, by a via 515, 516, respectively, that passes through the intervening insulator layer 424.

Figure 6:
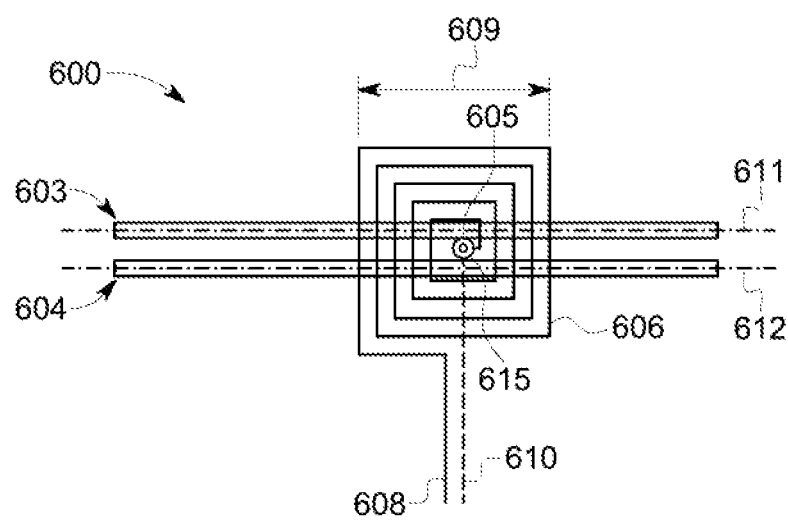
FIG. 6 is a diagram of an exemplary alternative embodiment of the eddy current sensor of FIG. 1.

FIG. 6 illustrates an alternative embodiment of an eddy current sensor 600. The eddy current sensor 600 includes a pair of drive conductors 603, 604 formed as a pair of parallel substantially straight conducting sections, and a sense coil 606 connected to electrical leads 608, 610. The embodiment illustrated in FIG. 6 operates and is constructed substantially the same as the exemplary embodiment of the eddy current sensor 100 of FIG. 1, except that the drive conductor 104 is formed as a pair of parallel conductors 603, 604 that are formed in a common conductor layer 426 (FIG. 4) of the multi-layer printed circuit. The drive conductors 603, 604, each comprise a longitudinal axis 611, 612, respectively. In one embodiment, the pair of drive conductors 603, 604 are positioned such that their longitudinal axes 611, 612, are equidistant from the axis 605 of the sense coil 606 at the point where the drive conductors 603, 604 are proximate to the sense coil axis 605.

As explained above in relation to the eddy current sensor 100 of FIG. 1, the sense coil 606 comprises a width 609, as measured at the outermost edges of the sense coil 606, and the drive conductors 603, 604 are formed in substantially straight parallel lines at least in the portions of the drive conductors 603, 604 that traverse the width 609 of the sense coil 606. The sense coil 606 may be formed as a single coil embodiment as described in relation to FIG. 3, wherein the sense coil 606 is electrically connected to electrical lead 610 formed in another conductor layer, e.g. layer 428 (FIG. 4) of the multi-layer printed circuit 400, by a via 615 that passes through an intervening insulator layer 424. Alternatively, the sense coil 606 may be electrically connected to a second sense coil formed in a separate conductor layer, e.g., layer 428, of the multi-layer printed circuit 400 by a via 615 that passes through the intervening insulator layer 424 (FIG. 4).

In view of the foregoing, embodiments of the invention provide a unique linear drive conductor that allows formation of an eddy current sensor with a small footprint and a self-nulling response that reduces noise. A technical effect is an improved inspection capability especially near an edge of a test object.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An eddy current sensor comprising:
    a first sense coil for detecting an eddy current, wherein the first sense coil comprises a first axis and a first width;
    a first drive conductor for inducing the eddy current, the first drive conductor spaced apart from the first sense coil by an insulator layer, wherein the first drive conductor comprises a substantially straight conducting portion that traverses the first width of the first sense coil; and
    a second sense coil electrically connected to the first sense coil,
    wherein the first axis of the first sense coil intersects the first drive conductor; and
    wherein the first sense coil, the second sense coil, and the first drive conductor are disposed in separate layers of the eddy current sensor, and wherein a second axis of the second sense coil intersects the first drive conductor.

2. The eddy current sensor of claim 1, wherein the first and second sense coils are electrically connected by a via through the insulator layer.

3. The eddy current sensor of claim 1, further comprising a third sense coil electrically insulated from the first sense coil, wherein the first sense coil and the third sense coil are disposed in a same layer of the eddy current sensor, and wherein a third axis of the third sense coil intersects the first drive conductor.

4. The eddy current sensor of claim 1, wherein the first sense coil comprises a square, planar coil.

5. An eddy current sensor comprising:
    a first plurality of sense coils for detecting an eddy current, wherein each of the first plurality of sense coils is disposed in a first layer of the eddy current sensor and arranged in a first row therein, each of the first plurality of sense coils comprising a first axis and a first width; and
    a first drive conductor for inducing the eddy current, wherein the first drive conductor is disposed in a second layer of the eddy current sensor and spaced apart from the first plurality of sense coils by an insulator layer, wherein the first drive conductor comprises a substantially straight conducting portion that traverses each of the first widths of the first plurality of sense coils in the first row,
    wherein each of the first axes of the first plurality of sense coils intersects the first drive conductor.

6. The eddy current sensor of claim 5, wherein each of the first plurality of sense coils comprises a square, planar coil.

7. The eddy current sensor of claim 5, further comprising:
    a second plurality of sense coils for detecting the eddy current, wherein each of the second plurality of sense coils is disposed in the first layer of the eddy current sensor and arranged in a second row therein, each of the second plurality of sense coils comprising a second axis and a second width; and
    a second drive conductor for inducing the eddy current, wherein the second drive conductor is disposed in the second layer of the eddy current sensor and spaced apart from the second plurality of sense coils by the insulator layer, wherein the second drive conductor comprises a substantially straight conducting portion that traverses each of the second widths of the second plurality of sense coils in the second row, and wherein each of the second axes of the second plurality of sense coils intersects the second drive conductor.

8. The eddy current sensor of claim 7, wherein each of the second plurality of sense coils comprises a square, planar coil.

9. An eddy current sensor comprising:
    a first sense coil for detecting an eddy current, wherein the first sense coil comprises a first axis and a first width;
    a first drive conductor for inducing the eddy current, the first drive conductor spaced apart from the first sense coil by an insulator layer, wherein the first drive conductor comprises a substantially straight conducting portion that traverses the width of the first sense coil on a first longitudinal axis;
    a second drive conductor for inducing the eddy current, the second drive conductor spaced apart from the first sense coil by the insulator layer, wherein the second drive conductor comprises a substantially straight conducting portion that traverses the width of the first sense coil on a second longitudinal axis; and
    a second sense coil electrically connected to the first sense coil,
    wherein the first drive conductor and the second drive conductor are positioned such that a longitudinal axis of each of the first and second drive conductor is equidistant from an axis of the first sense coil at a point where the first drive conductor and the second drive conductor are proximate the axis of the first sense coil.

10. The eddy current sensor of claim 9, wherein the first and second longitudinal axes are equidistant from the first axis of the first sense coil.

11. The eddy current sensor of claim 9, wherein the first sense coil comprises a square, planar sense coil.

12. The eddy current sensor of claim 9, wherein the first sense coil, the second sense coil, and the first and second drive conductors are disposed in separate layers of the eddy current sensor, and wherein the substantially straight conducting portions of the first and second drive conductors traverse the width of the second sense coil.

13. The eddy current sensor of claim 12, wherein the first and second sense coils are electrically connected by a via through an insulator layer.

14. The eddy current sensor of claim 9, wherein the first sense coil and the second sense coil are disposed in a same layer of the eddy current sensor, and wherein the substantially straight conducting portions of the first and second drive conductors traverse the width of the second sense coil.

\* \* \* \* \*